United States Patent [19]

Lee

[11] Patent Number: 5,024,099
[45] Date of Patent: Jun. 18, 1991

[54] PRESSURE TRANSDUCER WITH FLOW-THROUGH MEASUREMENT CAPABILITY

[75] Inventor: Shih-Ying Lee, Lincoln, Mass.
[73] Assignee: Setra Systems, Inc., Acton, Mass.
[21] Appl. No.: 439,617
[22] Filed: Nov. 20, 1989
[51] Int. Cl.$^5$ .............................................. G01L 9/12
[52] U.S. Cl. ........................................ 73/730; 73/724; 361/283
[58] Field of Search .................. 73/730, 724, 726, 727; 338/4; 361/283

[56] References Cited

U.S. PATENT DOCUMENTS

| | | | |
|---|---|---|---|
| 2,420,148 | 5/1947 | Ostergren | 73/730 |
| 3,046,788 | 7/1962 | Laimins | 338/4 |
| 4,207,551 | 6/1980 | Kautzky | 338/4 |
| 4,484,479 | 11/1984 | Eckhardt | 73/730 |

FOREIGN PATENT DOCUMENTS

WO88/04042  6/1988  European Pat. Off. ............. 73/730

Primary Examiner—Donald O. Woodiel
Attorney, Agent, or Firm—Wolf, Greenfield & Sacks

[57] ABSTRACT

A transducer measures the pressure of a fluid within a hollow conduit, typically one with a circular cross-section, having a central region that is deformed to a non-circular cross-section. This non-circular portion of the conduit displaces radially and repeatably without hysteresis in response to the pressure of the fluid in the conduit in a manner that corresponds to the pressure. A variable capacitor assembly, or a set of strain gauges mounted on the exterior of the non-circular portion, produce an electrical signal proportional to the radial displacement or to the strain, respectively. In one capacitive form, a pair of electrodes are mounted on opposite sides of the non-circular portion formed as free end portions of metallic sheet members with a central channel. In another capacitive form, electrodes are mounted at one or both ends of lever arms which in turn are coupled to the non-circular portion with a set of flexure plates to produce a mechanical amplification of the radial displacement.

25 Claims, 3 Drawing Sheets

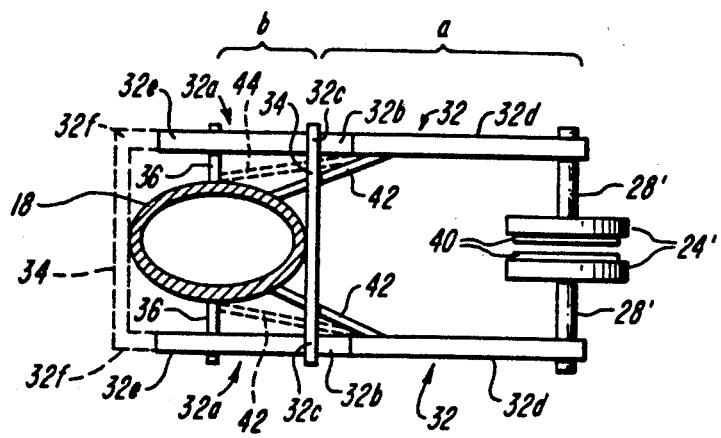
FIG. 4
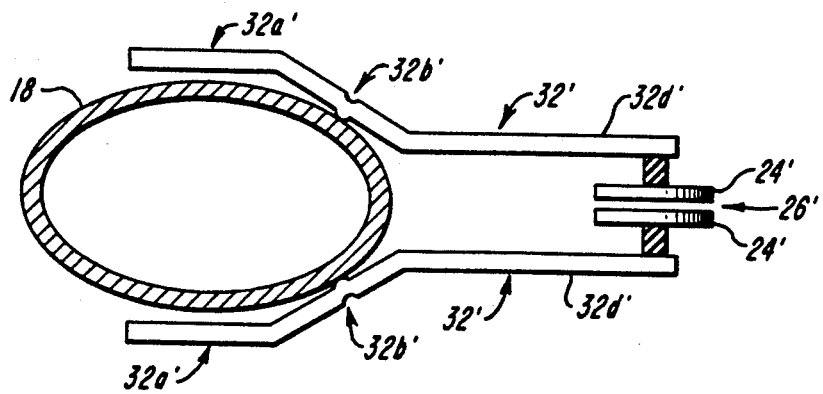
FIG. 5
FIG. 6
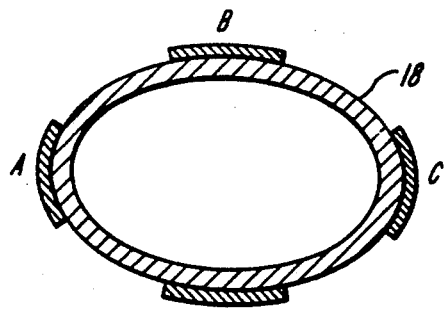
FIG. 7
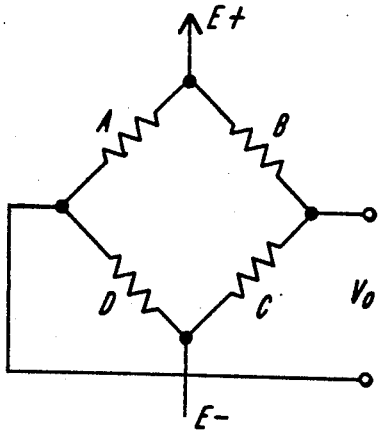
FIG. 8

PRESSURE TRANSDUCER WITH FLOW-THROUGH MEASUREMENT CAPABILITY

BACKGROUND OF THE INVENTION

This invention relates in general to pressure transducers, and more specifically to a flow-through pressure transducer with no internal dead space.

A wide variety of pressure transducers are known. In many transducers currently available, a fluid pressure acts on an edge mounted diaphragm. Movement of the diaphragm can then convert into an electrical signal using any of a wide variety of devices such as strain gauges, linear variable differential transformers and variable capacitors. U.S. Pat. Nos. 3,859,575 and 4,358,804 are examples of known capacitive pressure transducers of this general type.

Recently there has been a growing need to measure the pressure of a fluid flowing through a conduit, but without introducing any dead spaces in the conduit which can trap a portion of the fluid, collect contaminants, or, more generally, interfere with a smooth, laminar flow of the fluid. For example, in processing semiconductors it is important for process control to know the fluid pressure, but it is also necessary to maintain extreme purity of the fluids, even though different fluids may flow through the same conduit. To provide this extreme level of purity (to 1 part per billion), it has heretofore been necessary to dismantle the conduit and/or transducer manually, and then to clean all of the regions accessible to the fluids. This cleaning operation is costly and time consuming since the semiconductor manufacture is stopped during this cleaning. Similar considerations apply in other applications such as in the processing of foods and pharmaceuticals.

The conventional use of a pressure transducer for such process control applications has been to mount the transducer as a unit in an opening formed in the conduit, or onto a fitting mounted on the side of the conduit. In either case the transducer has a closed end and there is a dead space within the transducer where fluids can become trapped, as in small eddy currents, and non-fluid contaminants can collect.

One well known device for measuring such closed-end fluid pressure is the Bourdon tube. The tube is a closed-end conduit which is curved. Its open end is connected to the fluid whose pressure is to be measured. The application of a fluid pressure to the interior of the tube produces a hydraulic or pneumatic force which tends to straighten the tube. The degree of movement of the tip of the tube measures the applied fluid force. A limitation of the Bourdon tube is that because it has a closed end it cannot be used in flow-through situations. It is inherently non-compact and susceptible to thermal errors. Also, it has a large surface area exposed to the fluid, a large volume and is difficult to clean.

It is, therefore, a principal object of the present invention to provide a pressure transducer which can be operated both in a closed end mode or in a flow-through mode, but not restricted which has no internal dead spaces where fluid flowing through the transducer can stagnate and contaminants carried by the fluid can accumulate.

Another object of the invention is to provide a pressure transducer with the foregoing advantages which is also extremely accurate and reliable.

A further object of the invention is to provide a pressure transducer with the foregoing advantages in which the devices that transform a mechanical motion or strain into an electrical signal are readily replaceable.

Yet other objects of the invention include providing the pressure transducer with the foregoing advantages which has excellent operating characteristics such as a good vibration response, resistance to shock, good thermal response, and good hysteresis characteristics.

Still other objects of the invention include providing the pressure transducer with all of the foregoing advantages which also has a comparatively low cost of manufacture and which requires a relatively low level of skill to install.

SUMMARY OF THE INVENTION

A transducer that measures the pressure of a fluid in a system, typically a fluid flowing through a principal conduit, comprises a length of conduit with inlet and outlet portions, preferably ones having cross-sections of the same size and configuration as the principal fluid-carrying conduit itself. Disposed between the inlet and outlet portion is a length of the conduit which is deformed from the cross-sectional shape of the inlet and outlet portions to a non-circular cross-section. The interior surfaces of the conduit, including the non-circular portion and transitional regions extending from the non-circular portion to the inlet and outlet portions, are smooth to render the conduit free of stagnant regions or dead spaces which can retain a non-flowing portion of the fluid or collect contaminants.

The conduit is formed of a material type and thickness, and the deformation to a non-circular cross-section is of a magnitude such that, upon the application of an internal fluid pressure at the non-circular portion, the non-circular portion has a tendency to move elastically toward a circular shape. This change in cross-sectional shape produces a radial displacement of at least certain regions of the non-circular portion. The magnitude of the radial displacement corresponds to the pressure of the fluid within the conduit. This change also produces a surface stress (measured within the conduit wall in a direction transverse to the radial) and a corresponding surface strain in the wall sections of the non-circular conduit portion which also corresponds to the pressure of the fluid to be measured.

In a capacitive form of the present invention, the radial displacement of the non-circular portion is transmitted through a mounting assembly to at least one variable capacitor formed by a generally parallel, spaced apart pair of electrodes. The mounting assembly produces a change in the spacing between the electrodes which corresponds to the radial displacement of the non-circular section. In one form, the mounting assembly includes an opposed pair of plates with a central channel secured at their mid-point at diametrically opposed positions on the non-circular conduit portion at points of maximum radial displacement. The plates are preferably metallic and mounted on metallic posts that are secured to the outer surface of the non-circular portion of the conduit as by brazing, resistance welding, or a combination thereof. An insulator electrically isolates each plate from the associated post. The electrodes forming the variable capacitor are preferably a free end portion of the plates.

In another form, which can provide a mechanical motion amplification or reduction, electrodes are supported at the free ends of a pair of lever arms mounted on the outer surface of the non-circular conduit portion by first and second flexure plates. A first flexure plate extends between the lever arms, is mounted on the non circular portion, and provides a pivot point for the lever arms. A pair of second flexure plates extend between the non circular portion and the lever arm to mechanically transmit a radial displacement of the non-circular portion to the lever arms. In one form, the support also includes a pair of generally radially directed flexure plates which extend from the outer surface of the non-circular portion to the lever arms. They are oriented to resist a movement of the lever arms along their length to provide a better stability in response to shock and vibrational forces. In yet another form, each lever arm mounts an electrode on both of its ends to form a pair of variable gap capacitors operating in a push-pull mode. In this arrangement each electrode and an associated portion of its mount and lever arm counterbalances the electrode, mount and lever arm portion lying on the opposite side of the pivot point.

In yet another capacitive form, a pair of lever arms, also supporting at their free ends a pair of mutually spaced electrodes forming a variable capacitor, are connected at or near a point in the conduit wall which undergoes a maximum angular displacement. In this form, the lever arms are secured to the non-circular portion by brazing, spot resistance welding, or, preferably, by a combination of spot resistance welding and then brazing. This form of transducer can also be made with counterbalancing lever arm portions and electrodes to operate in a push-pull mode.

In a strain gauge form, at least one and preferably four strain gauges are secured to the outer surface of the non-circular portion of the conduit at a point of maximum surface stress, and therefore maximum surface strain, of the non circular portion as it deforms in response to an applied internal fluid pressure to be measured. With four strain gauges, they are preferably connected into a Wheatstone bridge circuit to produce an electrical output signal corresponding to the measured strain, and therefore corresponding to the applied internal fluid pressure.

These other features and objects of the present invention will be more readily understood from the following detailed description of the preferred embodiments which should be read in light of the accompanying drawings.

BRIEF DESCRIPTION OF THE DRAWINGS

FIG. 4 is a view in side elevation and partially in section, of the pressure transducer shown in FIG. 3;

FIG. 5 is a view in side elevation, and partially in section, corresponding to FIG. 4 of an alternative embodiment of a capacitive pressure transducer;

FIG. 6 is a highly simplified schematic view showing the non-circular conduit portion of the transducers shown in FIGS. 1–5 in an initial deformed non-circular state (solid lines) and in a radially displaced state (dashed line);

FIG. 7 is a view in vertical section of a pressure transducer according to the present dimension in a preferred strain gauge form utilizing four strain gauges mounted on the exterior surface of the non-circular conduit portion at positions of maximum surface stress and strain; and FIG. 8 is a highly simplified circuit schematic showing the four strain gauges of FIG. 7 arranged in a Wheatstone bridge circuit to produce an output signal indicative of the fluid pressure within the conduit.

DETAILED DESCRIPTION OF THE PREFERRED EMBODIMENTS

Figure 1:
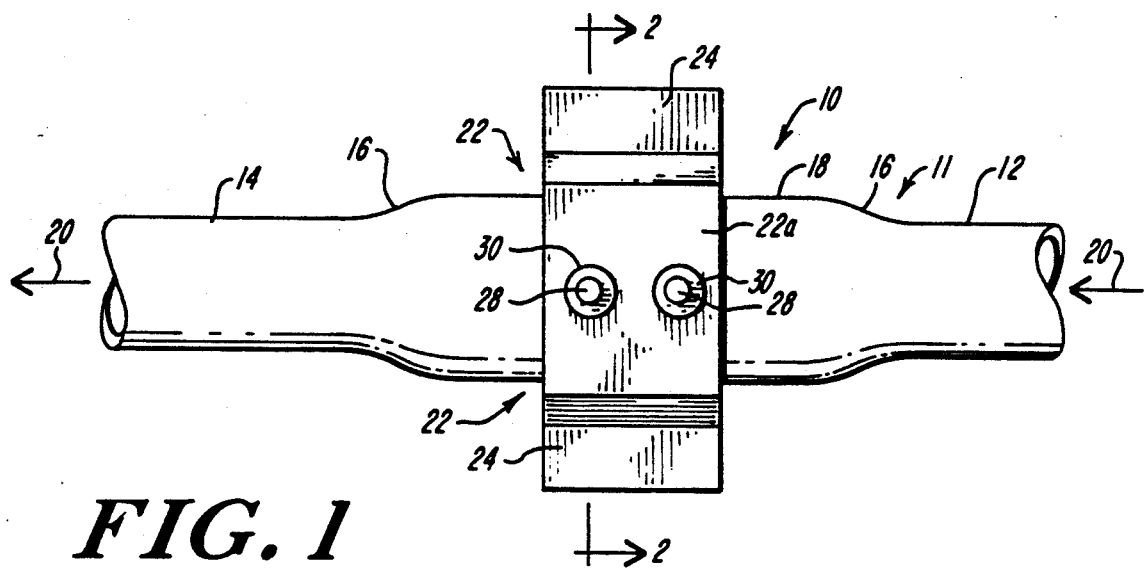
FIG. 1 is a top plan view of a flow-through pressure transducer according to the present invention in a capacitive form without motion amplification.
Figure 2:
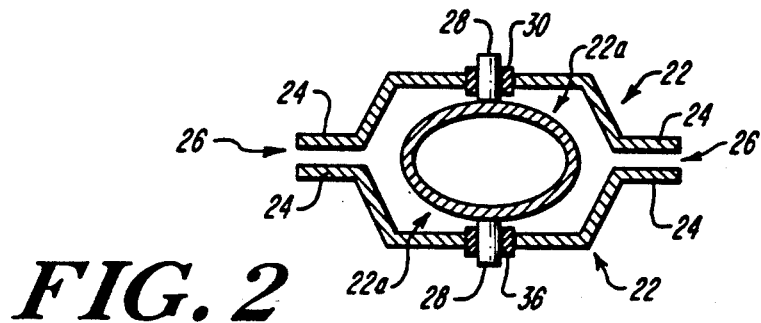
FIG. 2 is a view in vertical section along the line 2—2 in FIG. 1.

FIGS. 1 and 2 show a flow-through pressure transducer 10 according to the present invention which utilizes a conduit 11 having an inlet portion 12, an outlet portion 14, transition portions 16,16 and a non-circular portion 18 disposed between the transition portions 16,16. A fluid flowing through the conduit 11, as indicated by the arrow 20, applies a fluid pressure to the interior surface of the conduit. The conduit 11 is coupled into a system by butt-welding or low-contamination fittings such as the metal gasket fittings commonly termed "VCR". It is possible, however, that a main process fluid conduit itself can be the flow passage for the flow-through transducer of the present invention. The process fluid can be an ingredient in the processing of a pharmaceutical, foodstuff, or a fluid used in the manufacture of semi-conductor devices such as integrated circuits. The conduit is hollow and for most embodiments has a generally uniform wall thickness. The material forming the conduit is such that when a fluid pressure is applied to the non-circular portion 18, it will deform elastically in response to the fluid pressure tending to move to a circular configuration, which is the most stable configuration. Typically the conduit has a circular cross-section and the non-circular portion is formed by a mechanically deforming a short length of the conduit into a generally oval shape. Further, typically the non-circular portion originally has the same cross-sectional configuration and dimensions as the adjoining inlet and outlet conduit portions 12 and 14. While the invention will be shown and described principally with respect to a circular conduit with a non-circular portion 18 that is oval, it be understood that other cross-sectional geometries can be used such as a conduit which in its deformed state has a square, rectangular, or oval cross-section. Further, the non-circular portion can be a segment of the wall of a conduit, as for example, a wall portion of thin, generally uniform thickness formed in a generally square conduit with a circular internal passage, in cross-section, where one wall is machined from the outer surface from a flat to a cylindrical configuration mirroring that of the internal passage.

The material forming the conduit should have a yield strength sufficient to withstand the applied fluid pressures for the expected pressure range during operation. For certain applications where resistance to corrosion by the fluids carried in the conduits is an important consideration, it may be necessary to use certain inert materials which are characterized by a low yield strength. In those situations, increased strength due to an increase in the wall thickness of the conduit must be balanced against the necessity to have the circular cross-section deform to a sufficient degree to produce a reliably measured change. The motion-amplifying embodiments of the invention shown in FIGS. 3–5A are particularly useful in such situations. For general applications, it has been found that 316L stainless steel provides the desired degree of resistance to corrosion together with the desired elasticity, elastic memory, and yield strength. In addition, the material has a highly smooth finish which is free of minor nitches, crevices, or other irregularities. Also, the non-circular portion 18 is deformed to produce smooth interior contours both at the non-circular portion 18 and throughout the adjacent transition regions 16,16. The interior contours of the conduit 11 should result in a highly smooth, laminar flow 20 through the conduit 11.

A central aspect of the present invention is that after the conduit portion 18 is deformed from its original configuration, upon the application of an internal fluid force acting uniformly on the interior surface it tends to move elastically to a circular configuration. The forces applied by the fluid pressure to the non-circular portion 18 produce a radial displacement of the walls of the non-circular portion 18 over most of the tube and produces a maximum radial displacement along the minor elliptical axis, as best seen in FIG. 6. This radial displacement corresponds closely to the applied fluid pressure, and is therefore an accurate measurement of it at least to the same degree that a conventional edge mounted diaphragm produces a mechanical displacement which corresponds to an applied fluid pressure. The change in shape of the deformed portion 18 toward its original configuration also produces surface stress and strain in the walls of the tube with points of maximum stress and strain generally coinciding with points of maximum radial displacement of the walls of the portion 18. Therefore these points produce the best measure of the applied fluid pressure within the conduit 11.

The transducer 10 of the present invention also includes a mechanism for monitoring and electronically measuring the physical displacement or surface stress and strain of the non-circular portion 18 in response to the applied fluid force. The monitoring and measuring mechanisms described and illustrated are of both the capacitive and strain gauge type.

FIGS. 1 and 2 show a variable capacitance mechanism where a pair of support arms 22,22 preferably formed from a conductive sheet material support opposed pairs of electrodes 24,24 having a generally coplanar and horizontally extending orientation and mutually spaced to form a pair of variable capacitors 26,26 lying on opposite sides of the portion 18. The electrodes are preferably formed integrally with the support arms 22 as their free ends. The supports 22,22 each have a central channel 22a that straddles and surrounds the conduit portion 18 in a spaced relationship.

Posts 28 are resistance welded or otherwise secured to the outer surface of the non-circular portion 18, preferably at points of maximum radial displacement. If the posts are attached along the minor axis, as shown, the radial displacement is outwardly and the capacitance gap opens in response to an increase in the fluid pressure. If the posts are attached along the major axis, then the radial displacement is inwardly and the transducer is of the closing gap type. Each post mounts one of the support arms 22. Since the post is preferably metallic for attachment by resistance welding, an insulating ring 30 surrounds the post 28 and couples it to the associated support arm 22. The insulating ring 30 may be a bead of glass or any of a variety of other insulating materials known to those skilled in the art. Preferably, as best seen in FIG. 1, each support arm is mounted by a pair of posts spaced axially along the non-circular portion 18 to provide a greater stability for the support arm and an enhanced resistance to vibration and shock. The mounting arrangement for the electrodes 24,24 shown in FIGS. 1 and 2 produces a one-to-one correspondence between a radial displacement of the walls of the non-circular portion 18 and the change in the gap of the electrodes 24,24 forming the variable capacitors 26,26. It has been found that this configuration has a comparatively high signal to noise ratio and requires physical displacements of the conduit walls of a fairly large magnitude, e.g. 0.001 inch or more. This in turn requires that there be substantial fluid pressures within the conduit 11 to develop the necessary internal force and that the conduit wall thickness and material be selected to have a substantial yield strength. Therefore the arrangement illustrated in FIGS. 1 and 2 is best used for measurement in a low pressure range, e.g. less than 100 psi for a ¼ inch O.D. conduit with a wall thickness appropriate for the required strength and motion. Where it is not possible to utilize materials of considerable yield strength, or for operation in higher pressure ranges, it has been found preferable to utilize the electrode mounting arrangement shown in FIGS. 3, 4, 4A, 5 and 5A.

Figure 3:
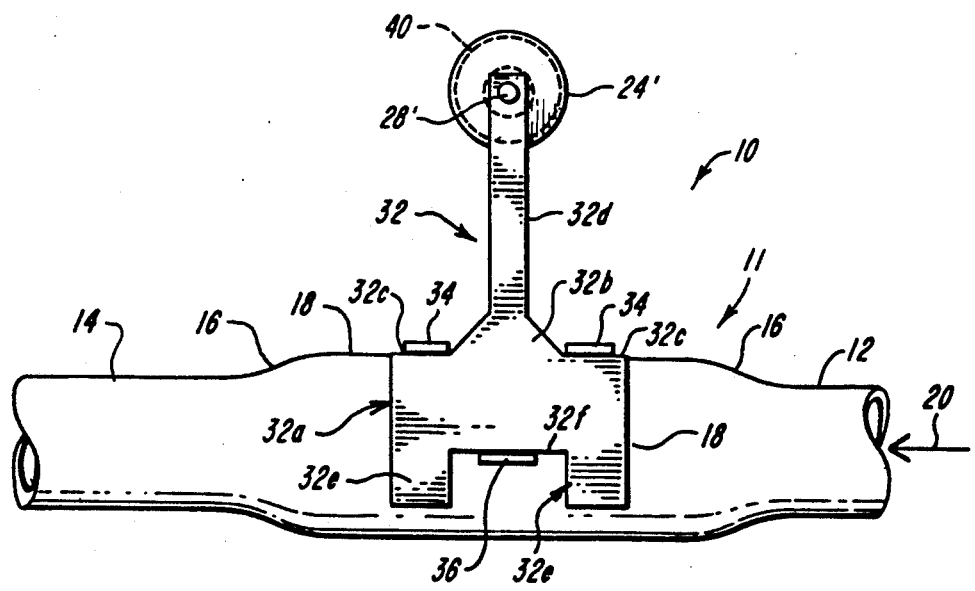
FIG. 3 is a top plan view of a pressure transducer according to the invention with the variable capacitor of the transducer having a lever arm support that provides motion amplification, or reduction, at the variable capacitor.

In the embodiment of FIGS. 3 and 4, the radial displacement of the walls of the non-circular portion 18 at a point of maximum radial displacement is transmitted to a pair of electrodes 24',24' mounted on the free ends of a pair of lever arms 32,32. First flexure plates 34,34 and a pair of second flexure plates 36,36 couple the lever arms, and therefore the electrodes, to the non-circular portion 18. The first flexure plates 34 extend across the portion 18 preferably at the end of a major axis and are tack welded and brazed, resistance welded, or otherwise secured at a midpoint of each flexure plate to the portion 18. The outer ends of the flexure plates 34,34 are then welded or otherwise rigidly secured to the lever arms 32,32. The first flexure plates provide a pivot point about which the lever arms 32,32 rotate. The flexure plates 34,34 are coplanar and preferably maintained in a coplanar relationship by a transverse connecting strip yielding an H-shaped flexure plate assembly.

To provide mechanical stability and counterbalance, the lever arms preferably have a widened base portion 32a which is generally coincident with, and in a parallel spaced relationship with, the non-circular portion 18. A transitional neck section 32b narrows from mounting flats 32c,32c of each base 32a to an elongated and comparatively narrow arm portion 32d. A mounting post 28' supports an electrode mounting plate 38, preferably formed from a dielectric material, which carries a ring of a deposited metalized surface 40 to serve as the conductive element of the variable capacitor electrode 24'. The post 28' is preferably located at the free end of each lever arm portion 32d.

As is best seen in FIG. 3, the lever arm base 32a has a cut-away portion 32e with a generally axially aligned mounting surface 32f which is rigidly coupled, as by spot resistance welding, to one end of one of the second flexure plates 36. The other ends of the flexure plates 36,36 are secured rigidly, as by tack welding and brazing, resistance welding, brazing, or otherwise to the outer surface of the non-circular portion 18, as is best seen in FIG. 4. Preferably, the point of attachment of the second flexure plates to the non-circular portion is at the point of maximum radial displacement of the non-circular portion. The second flexure plates are generally aligned with the direction of movement of the walls of the non-circular portion and therefore serve to transmit directly any movement of the walls to the lever arms. The lever arm base also includes portions 32e,32e which project beyond the mounting surface 32f. They serve to counterbalance the weight of the arm portions 32d and the electrodes 24',24'. The geometry is such that the center of gravity of the arm assembly coincides with the plane of flexure 34 to maximize resistance to shock and vibration.

Because the lever arms pivot about the first flexure plates 34,34, the motion transmitted by the second flexure plates is amplified, or reduced, by the ratio a/b where b, as shown in FIG. 4, is the distance from the point of attachment of the first flexure plate to the second flexure plate and a, also shown in FIG. 4, is the distance from the point of attachment of the first flexure plate to lever arm to the point of attachment of the electrodes 24',24'. (For the purpose of this description, "amplification" will be understood to include both amplification (a/b>1) and reduction (a/b<1), or even a ratio of a/b of 1.) It is usually preferable to have the ratio a/b be greater than 1 to produce an amplification of the motion of the walls of the non-circular portion 18. Because the variable capacitor is formed by a pair of electrodes which are opposed and which are both mounted on lever arms that move in response to displacements in the wall of the non-circular portion 18, any displacement of the wall is doubled. With the second flexure plates 36,36 secured along the minor axis of the non-circular portion, a fluid pressure increase produces an outward radial displacement, which in turn produces a closing gap capacitor. By mounting these plates along the major axis, an opening gap capacitor results.

The amount of amplification achieved with the FIG. 3-4 design is limited by the compactness of a required given application and the increase in susceptibility of the arm portions 32d to vibration and shock as they increase in length. Depending on the application, the increased thermal path resulting from a long lever arm formed of a conductive material may also introduce errors in the measurement. To assist in providing a better resistance to errors due to vibration and shock, auxiliary flexure plates 42,42 are preferably used. They extend generally radially to the lever arm portion 32d. Each plate 42 is secured at one end to the outer surface of the non-circular portion 18, or to the plates 36,36, as shown in phantom in FIG. 4. For ease of manufacture and assembly, the plates 42 preferably attach at and are integral with the plates 36,36. The opposite end of each flexure plate is rigidly coupled, as by resistance welding, to the lever arm portion 32d. The precise location and orientation is not critical as long as the plates 42,42 resist a movement in a direction parallel to the lever arms 32d,32d. With this arrangement, the motion sensing sub-assembly including the lever arms, flexure plates 32, and the electrodes, can be simply slipped onto the non-circular portion and welded to it as a unit.

Then, preferably, the flexure plates 36,36 with the arms 42,42 are assembled onto the mounted sub assembly. This provides a great convenience in assembly and reduces the cost of manufacture.

FIG. 5 illustrates an alternative, and presently preferred, embodiment of the FIG. 3-4 lever arm design, like parts being denoted with like reference numbers, but with an additional prime to signify a part which has been modified for the FIG. 5 embodiment. FIG. 6 illustrates in a highly simplified form the wall of the non-circular portion 18 in its deformed condition prior to the application of a fluid pressure in solid line, and in a changed form, moving toward a circular configuration, in dashed line. (The changed configuration in dashed line is shown in exactly a circular form for purposes of clarity. It will be understood, however, that the portion 18 will change in shape only slightly and will ordinarily not return fully to its original, undeformed circular form.) Points X and Y represent points of zero bending moment (points of inflection) of the wall. The points X and Y also represent a point of maximum angular displacement, represented by the angle $\theta$.

In FIG. 5, electrodes 24',24' are connected at the free end of lever arms 32',32' which are attached at a central point along their length to the outer surface of the non-circular conduit portion 18 along the points of inflection X and Y. This attachment can be, for example, by brazing, spot resistance welding or by a combination of these techniques where the arms are first spot welded, to secure a position and then brazed to provide additional mechanical strength at the point of attachment. Each lever arm 32' has a portion 32d' extending in parallel spaced relationship with the portion 32d' of the opposed lever arm 32' and mounting at its free end conductive plates and support posts, with suitable insulation, to form a variable capacitance transducer 26'. Each lever arm also includes an angled portion 32b' which is oriented generally along a tangent to the non-circular conduit portion at the point of maximum angular deflection. This mounting provides a clearance on either side of the point or line of attachment of the lever arm portion 32b' to the conduit portion 18 so as not to interfere with a rotational movement of the lever arm as the portion 18 changes shape in response to the applied fluid pressure.

Each lever arm 32' also includes a portion 32a' which in the preferred form extends generally parallel to the portion 32d' and spaced from the conduit portion 18. The base portions 32a' are not attached to the conduit, but preferably extend freely to counterbalance the arm portions 32d' and the accompanying electrodes. This counterbalancing minimizes the effect of external forces such as gravity, vibration and shock acting on the transducer which would otherwise tend to produce more significant errors in the variable capacitance gap which do not reflect changes in the cross-sectional configuration of the conduit portion 18.

Figure 4A:
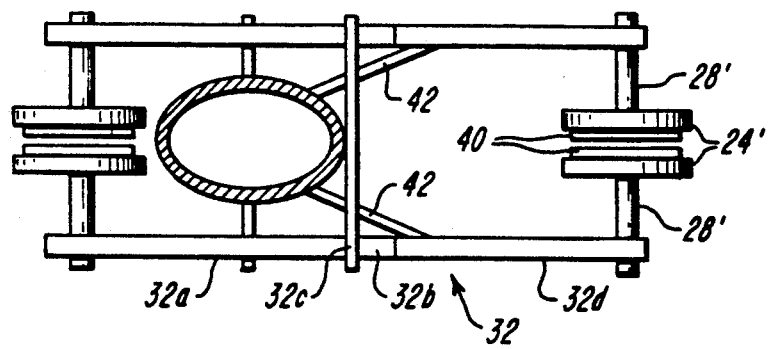
FIG. 4A is a view corresponding to FIG. 4 showing an alternative, push-pull embodiment of the transducer shown in FIGS. 3 and 4.
Figure 5A:
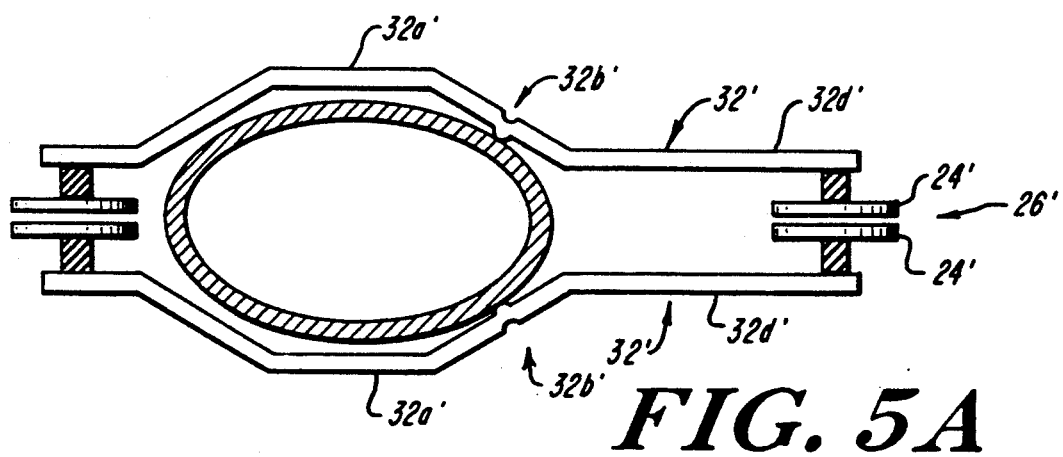
FIG. 5A is a view corresponding to FIG. 5 showing an alternative push-pull embodiment of the transducer shown in FIG. 5.

FIGS. 4A and 5A show alternative embodiments of the pressure transducers shown in FIGS. 4 and 5, respectively (like parts being identified with the same reference number). In the FIG. 4A and 5A embodiments, the arm portions 32a and 32a' extend beyond the non-circular portion 18 to mount an electrode 24' on a post 28', or a suitable insulating support such as a glass bead. An opposed pair of the electrodes 24' form a second variable capacitor 26' mounted on the arm portions 32a, 32a', preferably near the free end of the arm portion, as shown. Thus in both the FIGS. 4A and 5A embodiments, the lever arms 32 and 32' support a pair of variable capacitors mounted on opposite sides of the pivot point of the arms to produce a transducer operating in a push-pull mode. A pressure-responsive movement of the non-circular portion 18 moves the lever arms so that as one capacitor of the pair opens, the other closes. As is well known in the art, this mode of operation has many operational advantages such as a greater sensitivity and an output that is easier to linearize electronically than that of a single variable capacitor.

The push-pull embodiments of FIGS. 4A and 5A are also preferably constructed so that the center of gravity of each arm assembly coincides with the plane of flexure (defined by the first flexure plate 34 in FIG. 4A) or the point X or Y of maximum angular displacement. In any event, the second capacitor 26' and its associated mounts, such as the posts 28', and the lever arm portions 32a or 32a', acts as a counterbalance to the variable capacitor 26' and its associated mount and lever arm portion lying on the opposite side of the pivot point of the lever arms. This pivot arrangement provides an enhanced mechanical performance, particularly in response to shock and vibration. It should be noted, however, that these push-pull arrangements do not allow a simple "slip-over" assembly as with the FIG 3-4 embodiment, and therefore assembly is somewhat more complex and costly.

FIG. 7 shows a strain gauge embodiment of a flow-through pressure transducer according to the present invention. Four strain gauges A, B, C, and D are secured to the non-circular conduit portion 18, which is identical to the oval conduit portions described above with reference to FIGS. 1-5, at the major and minor axes of the cross section. The strain gauges are secured to the outer surface in a well-known manner to measure the surface stress, and the resultant of surface strain, of the conduit 18 over the adjacent regions of the conduit. For the oval configuration of the portion 18 shown in the preferred form illustrated in FIG. 7, the illustrated locations for the strain gauges A, B, C and D coincide with regions on the conduit portion 18 where there is a maximum of a tensile stress (adjacent strain gauges B and D), or a maximum of compressive stress (at strain gauges A and C). FIG. 8 shows a conventional Wheatstone bridge circuit configuration with the strain gauges A, B, C and D arranged in the bridge circuit so that they produce an output voltage signal indicative of the fluid pressure within the conduit portion 18.

There has been described a transducer which is responsive to and can be readily adapted to a variety of ranges of operation, has a comparatively low cost of construction, is readily assembled, presents a low risk of damage to the electronics during assembly or operation, is accurate and reliable in operation, and is more readily cleaned than known prior art, closed-end pressure transducers. When used in the preferred flow-through embodiment illustrated and described herein above, the present invention also provides extremely important advantage that it can provide all of the foregoing advantages while presenting no significant dead volumes within the transducer so that the transducer may be cleaned with a high degree of reliability without contaminating a subsequent fluid flow with material from a preceding fluid flow. Fluid flow purities with contaminant levels of 1 part per billion can be reliably and repeatably achieved. Even in non flow-through applications, certain of the foregoing advantages of the present invention make the present invention a competitive approach to pressure measurement.

Various alterations and modifications will occur to those skilled in the art from the foregoing detailed description of the invention and the accompanying drawings. For example, the first flexure plate or plates 34,34 could be secured between the base portions 32a,32a on the opposite side of the second flexure plates from the electrode as noted in dash line in FIG. 4. This arrangement produces a different class of lever, but will still produce motion amplification or reduction depending on the location of the pivot point and the relative length of the arms extending from the pivot to the load and the point of application of the force. A major disadvantage is that the electrodes and their support assembly cannot be simply slid over the non-circular portion prior to welding the electrode assembly in place onto the non-circular portion. Also, while the invention has been described with respect to a conduit 11 which has a fluid flowing through the conduit, it will be understood that the principles of the present invention can also be used for more conventional applications with less stringent operating requirements where the transducer has a closed end and is attached to the system using a conventional screw fitting or other known coupling arrangement. Such modifications and variations are intended to fall within the scope of the appended claims.

What is claimed is:

1. A transducer for measuring the pressure of a fluid in the transducer comprises
   a hollow conduit having (i) an inlet portion, (ii) a portion disposed adjacent said inlet portion formed by deforming said conduit to a non-circular cross-section and (iii) a first transition region extending between said non-circular portion and said inlet portion,
   the material forming said conduit having a tendency to displace radially from said non-circular cross-section toward a circular cross-section in response to the pressure of the fluid, the magnitude of said radial displacement and the surface stress and strain in at least a portion of said non-circular conduit corresponding to the pressure of the fluid,
   at least one pair of spaced apart electrodes forming a variable capacitor,
   means for mounting said electrodes to the exterior of said non-circular portion for converting said radial displacement into an electrical signal that corresponds to the fluid pressure through a corresponding movement of said mounting means and both of said electrodes.

2. The transducer of claim 1 wherein said conduit includes an outlet portion and a second transition region between said outlet portion and said non-circular portion to provide a flow-through capability for the fluid whose pressure is being measured,
   said conduit having smoothly contoured interior surfaces that render the conduit free of dead space.

3. The transducer of claim 1 wherein said mounting means is secured at the exterior of said non-circular portion at points of maximum relative linear motion of said radial displacement.

4. The transducer of claim 1 wherein said mounting means is secured at the exterior of said non-circular portion at points of maximum angular motion of said non-circular portion.

5. The transducer according to claim 1, 3, or 4 wherein said mounting means comprises a pair of rigid lever arms, means for mounting one of said electrodes at one end of each of said lever arms, and means for coupling said lever arms to the exterior of said non-circular portion to translate said radial displacement into a corresponding angular movement of said lever arms about said non-circular portion.

6. The transducer according to claim 5 wherein said coupling means is secured to said lever arms to produce a mechanical amplification of said radial displacement at said electrodes.

7. The transducer according to claim 6 wherein said coupling means comprises (i) at least one first flexure plate that is secured between said levers arms and (ii) at least two second flexure plates each secured between said non-circular portion and said lever arm, with the said point of said securing of said second flexure plates lies on the opposite side of said at least one first flexure plate with respect to said electrode, whereby said radial displacement is transmitted to said lever arms by said at least two second flexure plates and produces a pivoting of lever arms about said at least one first flexure plate.

8. The transducer according to claim 7 wherein there are multiple first flexure plates and they are coplanar.

9. The transducer according to claim 7 wherein said at least one first flexure plate is secured to said non-circular section at its midpoint.

10. The transducer according to claim 7 wherein said mounting means includes two auxiliary flexure plates each and at the other end to one of said lever arms.

11. The transducer according to claim 5 wherein said electrode mounting means comprises a dielectric plate mounted on a post supported on a free end of said lever arm.

12. The transducer according to claim 5 wherein said at least one pair of spaced apart electrodes comprises a first pair of electrodes mounted at said one end of each of said lever arms and a second pair of electrodes mounted at the opposite end of each of said lever arms to form a pair of variable capacitors operating in a push-pull mode.

13. The transducer according to claim 12 wherein said lever arms are coupled to said non-circular portion at a position such that said capacitors and their associated mounting means and the adjacent portion of the associated ones of said lever arms counterbalance one another.

14. The transducer according to claim 13 wherein said coupling position coincides with the center of gravity of each said lever arm and said mounting means and electrodes secure to it.

15. The transducer according to claim 5 wherein said non-circular portion has an oval cross-section and said mounting means comprises means for securing said lever arms directly to said non-circular portion at points of maximum angular deflection.

16. The transducer of claim 15 wherein each of said lever arms have an arm portion lying on opposite sides of the associated point of maximum angular displacement to provide a counterbalance and the length of said lever arm portions mounting said electrodes provides a mechanical amplification of said maximum angular defection.

17. The transducer of claim 16 wherein said at least one pair of spaced apart electrodes comprises a first pair of electrodes mounted at said one end of each of said lever arms and a second pair of electrodes mounted at the opposite end of each of said lever arms to form a pair of variable capacitors operating in a push-pull mode.

18. The transducer of claim 16 wherein said lever arms are coupled to said non-circular portion at a position such that said capacitors and their associated mounting means and the adjacent portion of the associated ones of said lever arms counterbalance one another.

19. The transducer of claim 16 wherein said couplinq position coincides with the center of gravity of each said lever arm and said mounting means and electrodes secured to it.

20. The transducer of claim 1 wherein said mounting means comprises two support arms mounted on said non-circular portion in a diametrically opposed relationship.

21. The transducer of claim 20 wherein said support arms carry said electrodes at one end and are counterbalanced at the other end.

22. The transducer of claim 20 wherein said support arms each have a channel formed at their center adapted to surround said non-circular portion in a spaced relationship except for the point of said mounting.

23. The transducer of claim 22 further comprising mounting means including at least one post secured to the exterior of said non-circular portion, and an insulating ring secured on said at least one post and mounting an associated one of said support arms.

24. The transducer of claim 23 wherein there are plural posts arrayed generally along the longitudinal axis of said non-circular portion.

25. The transducer of claim 20 wherein said support arms are metallic and said electrodes comprise the free ends of said support arms.

* * * * *